United States Patent
Merza et al.

(10) Patent No.: US 10,024,746 B2
(45) Date of Patent: Jul. 17, 2018

(54) INLINE PRESSURE TRANSDUCER

(71) Applicant: GYRUS ACMI, INC., Southborough, MA (US)

(72) Inventors: Saeed Merza, Cordova, TN (US); Joey Magno, Cordova, TN (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 15/348,085

(22) Filed: Nov. 10, 2016

(65) Prior Publication Data

US 2018/0125599 A1    May 10, 2018

(51) Int. Cl.
*G01L 9/00* (2006.01)
*A61B 90/00* (2016.01)
*G01L 9/08* (2006.01)

(52) U.S. Cl.
CPC ............ *G01L 9/0001* (2013.01); *A61B 90/06* (2016.02); *G01L 9/08* (2013.01); *A61B 2090/064* (2016.02)

(58) Field of Classification Search
CPC ......... G01L 9/0001; G01L 7/02; G01L 23/10; G01L 9/0002; G01L 9/0005
See application file for complete search history.

(56) References Cited

U.S. PATENT DOCUMENTS

| | | | |
|---|---|---|---|
| 3,149,492 A | 9/1964 | Weinberg | |
| 4,090,440 A | 5/1978 | Jensen | |
| 4,194,401 A | 3/1980 | Claassen et al. | |
| 4,304,126 A | 12/1981 | Yelke | |
| 4,391,147 A | 7/1983 | Krempl et al. | |
| 5,031,460 A | 7/1991 | Kanenobu et al. | |
| 5,524,475 A * | 6/1996 | Kolpak | G01N 29/036 |
| | | | 73/19.03 |
| 2004/0167735 A1* | 8/2004 | Rothman | G01F 1/363 |
| | | | 702/100 |
| 2006/0144155 A1* | 7/2006 | Liu | A61B 5/02152 |
| | | | 73/753 |

* cited by examiner

*Primary Examiner* — Harshad R Patel
*Assistant Examiner* — Brandi Hopkins
(74) *Attorney, Agent, or Firm* — The Dobrusin Law Firm P.C.

(57) ABSTRACT

A method of determining fluid pressure inside a conduit. The method includes positioning a conduit in a surgical system. The conduit having an external surface, and the surgical system having a pair of sensors. The conduit is positioned in the surgical system such that the external surface of the conduit applies a force on the pair of sensors when the conduit expands. The method includes a step of generating one or more electrical signals with the pair of sensors. The one or more electrical signals corresponding to the force on the pair of sensors. The method includes a step of determining the fluid pressure inside the conduit by converting the one or more electrical signals into a fluid pressure value through a controller.

20 Claims, 4 Drawing Sheets

INLINE PRESSURE TRANSDUCER

FIELD

These teachings relate to a surgical system and apparatus for determining fluid pressure inside a conduit.

BACKGROUND

During a surgical procedure, fluid, such as water or air, can be supplied from a fluid source through one or more conduits to a patient or into a surgical site. The fluid can be introduced into the surgical site for a variety of reasons, such as, for example, to enable joint distention, provide a clear view of the surgical site, and/or extract debris resulting from mechanical debriding, coagulation and ablation, or through the use of ultrasonic devices.

Current technology for determining fluid pressure in the one or more conduits includes using a disc-shaped diaphragm member that is assembled into a cassette and located on the downstream side of the conduit before the fluid enters the patient or the surgical site. Once the fluid in the conduit is pressurized, the diaphragm member expands and the resultant force is held against a load cell. The load cell sends an electric signal to a controller that convers the electric signal into a pressure value. The cassette including the diaphragm member is part of the conduit, and after the surgical procedure the cassette and diaphragm member are disposed with the conduit.

As may be readily apparent, the current technology requires multiple components (i.e., diaphragms, load sensors, cassettes), which may increase the cost and complexity for determining the pressure of fluid in a conduit. The current technology may also be prone to pressure spikes that are generated by the pulsations of a peristaltic pump because the diaphragm to load cell setup is extremely sensitive. Therefore, these systems may require electronic filtering schemes to reduce the pressure spikes, which may undesirably add cost and complexity to the system. Also, properly assembling the cassette and diaphragm may be time consuming and cumbersome, which may undesirably add time to surgical procedure. Moreover, disposing of the cassette and diaphragm member after every surgical procedure is costly and wasteful.

It may therefore be desirable to improve the current state of the art. For example, it may be desirable to have a system and method for quickly, easily, and accurately determining fluid pressure inside a conduit. It may be desirable to have a system that allows for a conduit to be quickly and easily installed in the system and removed from the system. It may be desirable to have a system for determining fluid pressure in a conduit that can be reused for multiple surgical procedures

SUMMARY

These teachings provide a system and method for quickly, easily, and accurately determining fluid pressure inside a conduit. Advantageously, a conduit can be quickly and easily installed and removed from the system according to the teachings herein. The system according to these teachings can be reused for multiple surgical procedures, which may desirably reduce cost and waste.

These teachings provide a method of determining fluid pressure inside a conduit. The method includes positioning a conduit in a surgical system. The surgical system comprising a pair of sensors. The conduit is positioned, attached, or installed in the surgical system such that an external surface of the conduit is against the pair of sensors so that when the conduit expands, the external surface of the conduit applies a force on the pair of sensors. The method includes generating one or more electrical signals with the pair of sensors. The one or more electrical signals correspond to the force applied by the external surface of the conduit on the pair of sensors after the fluid pressure inside the conduit is increased. The method includes determining with a controller the fluid pressure inside the conduit by converting the one or more electrical signals into a fluid pressure value.

These teachings provide a surgical system. The system includes a pair of sensors and a controller. A conduit is attached to the surgical system such that an external surface of the conduit is placed against the pair of sensors so that when the conduit expands, the external surface applies a force on the pair of sensors. After fluid pressure is increased inside the conduit, the increase in the fluid pressure causes the conduit to expand such that the external surface applies the force on the pair of the sensors. The pair of sensors generate one or more electrical signals. The one or more electrical signals are communicated to the controller, which converts the one or more electrical signals into a fluid pressure value.

These teachings provide a method of determining pressure of a fluid in a conduit. The method includes attaching the conduit to a surgical system. The system includes a first sensor; a second sensor; a first force transferring member; and a second force transferring member. The method includes determining the pressure of the fluid in the conduit. The conduit is configured to expand in response to an increase in the pressure of the fluid in the conduit. The expanding conduit increases an initial force applied by the conduit on both the first force transferring member and the second force transferring member. The increased force is transferred from the first force transferring member to the first sensor and front the second force transferring member to the second sensor. One or more electrical signals corresponding to the increased force transferred to both the first sensor and the second sensor are communicated from the first sensor and the second sensor to a controller, the controller corresponds the one or more electrical signals to the pressure of the fluid in the conduit.

These teachings provide a method of determining fluid pressure inside a conduit. The method includes positioning a conduit in a surgical system. The conduit having an external surface, and the surgical system having a pair of sensors. The conduit is positioned, attached, installed, or located in the surgical system such that the external surface of the conduit applies a force on the pair of censors when the conduit expands. The method includes a step of generating one or more electrical signals with the pair of sensors. The one or more electrical signals corresponding to the force on the pair of sensors. The method includes a step of determining the fluid pressure inside the conduit by converting the one or more electrical signals into a fluid pressure value through a controller.

These teachings provide a surgical system, comprising a pair of sensors; and a controller. A conduit is attached to the surgical system such that an external surface of the conduit is placed against the pair of sensors so that when the conduit expands, the external surface applies a force on the pair of sensors. The pair of sensors generate one or more electrical signals from the force on the pair of sensors. The one or more electrical signals are communicated to the controller, and the controller converts the one or more electrical signals into a fluid pressure value.

DETAILED DESCRIPTION

Figure 1:
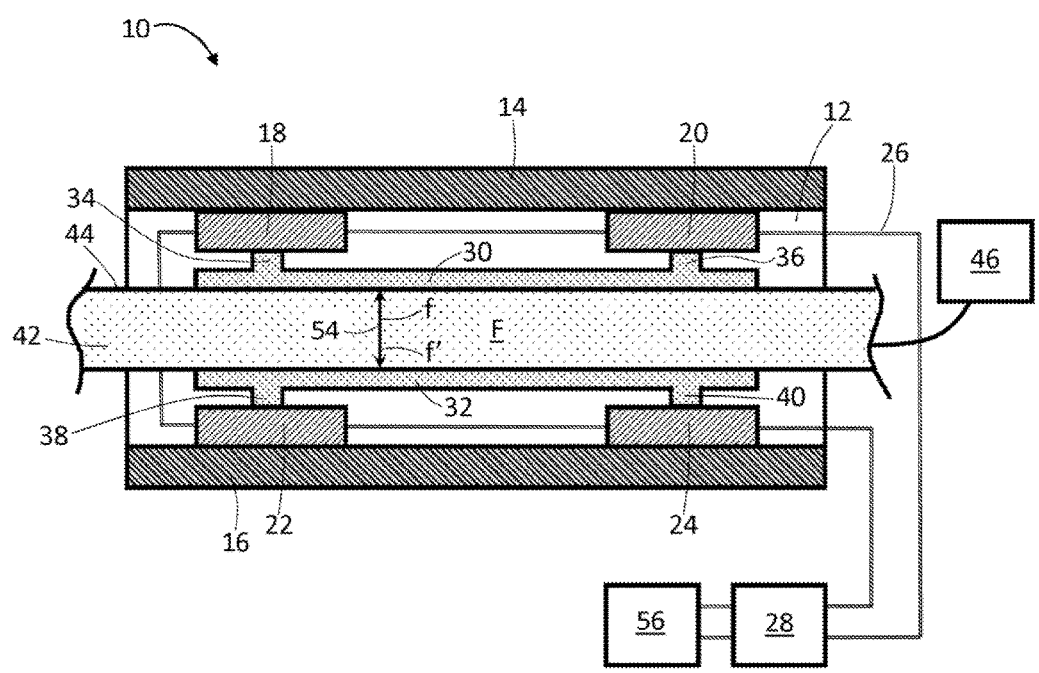
FIG. 1 is a schematic of the system according to the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

System. These teachings relate to a system. The system may be used in a non-surgical setting for determining fluid pressure in a conduit. For example, the system may find use in various automotive, industrial and/or manufacturing applications. The system may be a surgical system for determining fluid pressure in a conduit. The system may be used in a surgical setting for determining fluid pressure in a conduit before the fluid enters a patient or surgical site. The system may be used to determine a change (i.e., an increase and/or a decrease) in the fluid pressure in a conduit. The system according to the teachings herein may be used in concert with other systems, such as a fluid management console, one or more pumps, and/or one or more fluid supply for determining the pressure of fluid supplied to or passing through one or more conduits. For example, the system may be attached to an outer surface or an inner surface of a fluid management console, a fluid supply or a pump. The system, described herein may include one or more of the features or components described herein. However, it is understood that one or more of the features described herein may be omitted from the system.

The system advantageously provides for a user to quickly, easily, and accurately determine the fluid pressure inside a conduit. A conduit can be quickly and easily installed and removed from the system without requiring complicating routing or positioning of the conduit in the system. Because the system is not permanently connected to the conduit, the system can be reused for multiple procedures. Moreover, because the system does not directly contact the fluid passing through the conduit, the system can be reused for multiple surgical procedures without sterilizing the system. Of course, the system can be sterilized, such as by placing the system in an autoclave.

Base. The system includes a base. The base may support the one or more components of the system. The base may be generally planer. The base may be part of another device, which the system is incorporated into. For example, the base may be a surface or feature of the fluid management console or fluid source. In that regard, the one or more features of the system (i.e., the one or more sensors, controller, force transmitting members, or a combination thereof) may be added to or supported by one or more surfaces of the fluid management console or fluid source.

Walls. The system may include one or more walls. The walls may support the one or more sensors, the force transmitting members, or both. One or more of the walls may be part of another device, which the system is incorporated into. For example, one or more of the walls may be a surface or feature of the fluid management console or fluid source. In that regard, the one or more features of the system (i.e., the one or more sensors, controller, force transmitting members, or a combination thereof) may be added to or supported by one or more walls of the fluid management console or fluid source.

Power Source. The system may include a power source, or may be connected to a power source. The power source may function to power the one or more components of the system, such as the one or more sensors, the controller, and/or the display. The power source may be an AC power source, a DC power source, or both. The power source may be incorporated into the system, or the power source may be past of another system, such as fluid management console.

Sensor. The system includes one or more sensors. The sensor may function to read, react, and/or respond to a change (i.e., increase and/or decrease) in the fluid pressure in the conduit. The sensor may function to generate one or more electronic signals in response to the change in the fluid pressure in the conduit. The sensor may send or transmit the one or more electronic signals to a controller for processing and/or determining the fluid pressure in the conduit. The sensor may be a force collector (i.e., a diaphragm, piston, bourdon tube, or bellows) that measures strain or deflection on the sensor due to an applied force on the sensor by an expanding or contracting conduit when the pressure of the fluid in the conduit correspondingly increases or decreases. The sensor may be a piezo-resistive strain gauge or sensor. The sensor may be a transducer that converts pressure variations applied on the sensor into one or more electronic signals. The sensor may be a flexible printed circuit sensor. The sensor may be a FLEXIFORCE™ sensor, available for Tekscan, Inc. which is shown and described in https://www.tekscan.com/product-group/embedded-sensing/force-sensors, last accessed on Nov. 2, 2016. One or more of the sensors may be connected to form a Wheatstone bridge circuit so that the one or more electrical signals from the sensors is maximized and errors is reduced.

The system may include any number of sensors. The sensors may be supported on the base, the one or more walls, or both. The sensors may be sandwiched between the one or more walls and the force transmitting member. Alternatively, the sensors may be sandwiched between the one or more walls and the conduit. It is understood that while the figures illustrate four sensors (refs. 18, 20, 22, 24), the system may include more than four sensors, or less than four sensors. For example, the system may include one or more sensors on each side of the conduit, two or more sensors, three or more sensors, four or more sensors, etc. Increasing the number of sensors in the system may increase accuracy and/or redundancy. The system may include the same number of sensors on each side of the conduit. The system may include a different number of sensors on each side of the conduit. For example, one side of the conduit may include two or more sensors and the other side may include one sensor, or three or more sensors. The one or more sensors may be located directly across from one another such as shown in the configurations illustrated in FIGS. 1-3, or the sensors may be staggered apart from opposing sensor(s), such as the configuration shown in FIG. 4. Of course, the system may include a combination of one or more sensors that are located directly across from one another and one or more of the sensors that are staggered from one another.

The one or more sensors may be electronically connected via one or more conductor wires. Wiring of the sensors may be accomplished in a variety of configurations. For example, all of the sensors may be electrically connected in series to the controller (for example, as illustrated in FIG. 1) with a single conductor wire. Such a configuration, as illustrated in FIG. 1, may be advantageous because measurement accuracy can be increased. However, in the configuration illustrated in FIG. 1, if one or more sensors or the conductor wire fails, no electrical signals will be transmitted to the controller.

Figure 2:
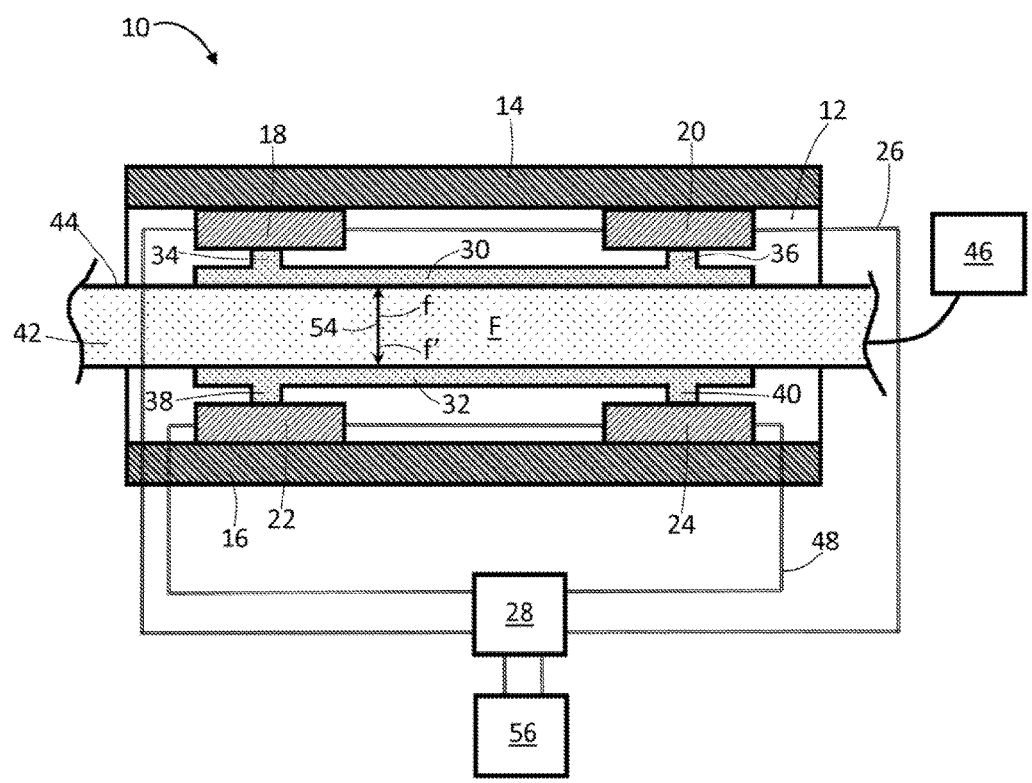
FIG. 2 is a schematic of the system according to the teachings herein.

In another wiring configuration, two or more sensors may be electrically connected in a sensor grouping and electrically connected in series with the controller via a single conduct line. The system may include two or more of such sensor groupings. For example, FIG. 2 illustrates two sensors (refs. 18, 20 electrically connected in series in a first sensor grouping with the controller with a single conductor wire, and two other sensors (refs. 22, 24) electrically connected in series a second sensor grouping with the controller. Such a configuration may be advantageous if one more of the sensors in a sensor grouping fail, electrical signals may still be obtained from the other sensor grouping and transmitted to the controller for determining fluid pressure in the conduit. Such a configuration may increase measurement accuracy by having two (or more) sensors in each grouping. Also, such a configuration illustrated in FIG. 2 may increase measurement redundancy by having two (or more) groupings of sensors. Of course, it is also envisioned that two or more of the sensors may be electrically connected in series in a sensor grouping with the controller, while a fourth sensor is directly connected to the controller with a separate conductor wire.

Various other wiring configurations are possible and within the scope of this disclosure. For example, one or more sensors may be electrically connected in parallel with another sensor(s). Electrically connecting sensors in parallel may be advantageous if, for example, a sensor or conductor wire fails, subsequent sensors can detect pressure changes and generate the electronic signals.

Force transmitting member. The system may include one or more force transmitting members. The force transmitting member may function to transfer one or more forces applied on the force transmitting member resulting from the expansion or contract of the conduit to the one or more sensors. The force transmitting member may function to uniformly apply a static force on the one or more sensors during a fluid pressure change in the conduit.

Figure 3:
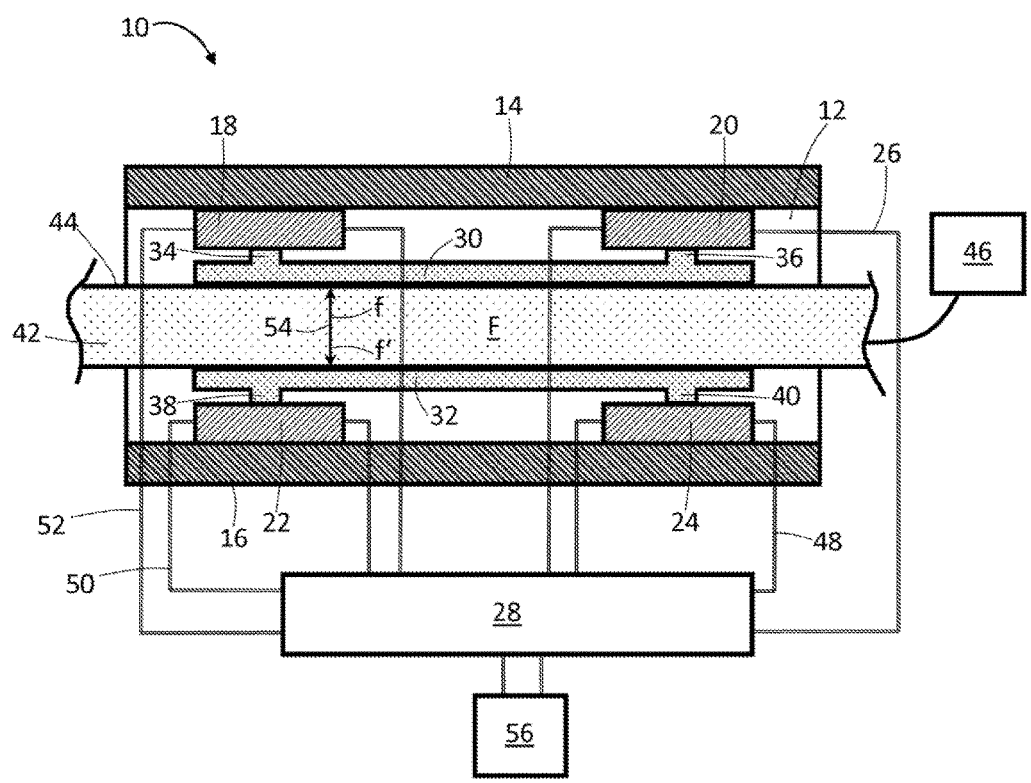
FIG. 3 is a schematic of the system according to the teachings herein.

A force transmitting member may be in communication with each of the sensors. Alternatively, the system may include a force transmitting member in communication with two sensors, for example, as illustrated in FIGS. 1-3. The system may include two or more force transmitting members that are located on each side of the conduit (i.e., approximately 180 degrees apart). In some configurations, the system may include two or more force transmitting members that are located less than or greater than 180 degrees apart. When the conduit is positioned, attached, located, or installed in the system, the conduit may be in contact with or slightly pinched by one or more of the force transmitting members. This contact or pinch may be taken into consideration and/or compensated for when determining the fluid pressure in the conduit. For example, the contact or pinch may cause the force transmitting member(s) to apply a slight force on the one or more sensors before any fluid is actually provided to the conduit and/or pressurized in the conduit. The controller may be adapted to understand that this slight pinch and/or contact is a zero-pressure condition in the conduit. Then, after the fluid is supplied to the conduit and/or pressurized in the conduit, further movement of the force transmitting member against the sensors due to the expansion of the conduit may be used to determine the fluid pressure in the conduit. The aforementioned description may also apply to systems that are free of one or more force transmitting members. That is, when the conduit is initially placed in the system during a zero-pressure condition, the conduit may be in directly in contact with or slightly pinched by one or more sensors. The controller may be adapted to understand that this slight pinch and/or contact is a zero-pressure condition in the conduit.

The force transmitting member may be an elongated member or mandrel. A length or longitudinal axis of the force transmitting member may be substantially and generally parallel with a longitudinal length or longitudinal axis of the conduit. The force transmitting member may be in contact with a tangent of the conduit. The force transmitting member may extend at least partially around the conduit. The force transmitting member may extend completely around the conduit. However, as was briefly discussed above, one or more of the force transmitting members may be omitted, and the conduit may be positioned, attached, installed, or located in the system against one or more of the sensors.

The force transmitting member may be adapted to float. The force transmitting member may be adapted to float to avoid any friction with other features of the system that may cause misleading or erroneous sensing of the electronic signals from the sensors. The floating may be accomplished by allowing the force transmitting members to hang on the one or more conduits or through the use of magnets to repel the force transmitting members from touching any adjacent sides of the system (i.e., the walls). Repulsion happens between like poles of the permanent magnets. In this case, the force transmitting member may be made out of a permanent magnet. Since the sides in contact with the tubing and its opposing side contacts the force sensors are already constrained, the only sides that requires this levitation action is the top and bottom sides of this component. This will be designed it such a way that the magnets on the top and bottom are property constrained so they do not flip over and become attracted to the force transmitting member. In addition, the magnetic repulsion force direction will be perpendicular to the expansion force acting on the sensors. The purpose of this feature is not to have any external contact that may cause friction except the tubing and force sensors, and affect the force reading on the aforementioned force sensors. It also prevents magnetic force repulsion effect on the sensor.

Projection. The force transmitting member may include one or more projections. The one or more projections may junction to transfer one or more forces applied on the force transmitting members resulting from the expansion of the conduit to the one or more sensors. The projection may be a projection, a barb, an extension, or the like. The projection may be located on one or more of the sensors and extend into contact with the force transmitting member and/or conduit.

Controller. The system may include one or more controllers. The controller may function to determine the fluid pressure inside the conduit. The controller may determine the fluid pressure inside the conduit by converting the one or more electrical signals received from the one or more sensors into a fluid pressure value. The controller may use a look-up table to convert the one or more electrical signals into a fluid pressure value. The controller may have a memory to store a look-up table and/or one or more values or equations for determining the fluid pressure inside the conduit. The correlation of the one or more electrical signals to a particular fluid pressure value may be linear. The controller may use one or more algorithms, computers, processors, or a combination thereof to determine the fluid pressure value. The controller be a computer, processor, or a combination thereof to perform one or more of the functions described herein, including determining the fluid pressure value. The controller may be in electrical commination with a display for displaying the determined fluid pressure. The controller may be in electrical commutation with a fluid source for automatically increasing or decreasing the pressure in the conduit based on a preset or desired pressure value. The controller may be part of the system, or the controller may be part of the fluid management console. In this regard, the system may include a plug for communicating the one or more electrical signals to the controller in the fluid management console for determining the fluid pressure.

Display. The system may include one or more displays or may be in communication with one or more displays. The display may function to visually display a determine fluid pressure inside the conduit. The determined fluid pressure value may be transmitted to the display wirelessly, or along one or more conductor wires. The display may be part of the system, or the display may be part of another system, such a fluid management console. In this regard, the system may include a plug for communicating the determined fluid pressure from the controller or system to the display in the fluid management console.

Fluid source. The system may be in communication with a fluid source. The fluid is preferably an uncompressible fluid, such as air or water or saline. The fluid source may be a bag of saline fluid. The fluid source may be a source of air. The fluid source may be part of the system, or may be in communication with the system. The fluid source may be contained in a fluid management console.

The fluid source may include a device for moving the fluid from the source to the conduit. The device may increase the pressure of the fluid in the conduit. The device may decrease the pressure of the fluid in the conduit. For example, the device may be a suitable pump. The device may be a peristaltic pump or centrifugal pump. The device may be gravity feeding the fluid to the conduit.

During use, an increase in the pressure of the fluid in the conduit may cause the conduit to expand. The expansion may be generally radially. The expansion may be generally uniform around a circumference of the conduit. However, in some instances, the expansion of the conduit may not be uniform. This may occur when the thickness or durometer of the conduit is not uniform or if air pockets or bubbles are in the fluid. In these cases, the forces (e.g., f and f' in the figures) applied by the expanding conduit on the force transmitting members and/or sensors may be different.

Conduit. The system may include one or more conduits. The conduit may function to transfer or supply a passageway for fluid to be moved form a fluid source to a destination, such as a patient, or surgical site. The conduit may include a suitable durometer that expands and contracts as a result of a change in pressure of a fluid being moved therethrough. A circumference and or diameter of the conduit may expand when the fluid is pressured in the conduit. The circumference and/or diameter of the conduit may expand in proportion to an increase in the fluid pressure in the conduit. The circumference and/or diameter of the conduit may contract in proportion to a decrease in the fluid pressure in the conduit. The conduit may be constructed from a suitable plastic, rubber, or medical grade tubing. The conduit may be constructed from a medical grade PVC material. The conduit may have a single passageway, or the conduit may have multiple passages (i.e., multi-passage conduit). The conduit may be transparent or non-transparent.

Method. Determining the fluid pressure in the conduit can be accomplished according to a method. It is understood that the following method steps can be performed in virtually any order. It is also understood that one or more steps disclosed throughout this entire disclosure can be used in the method. The method includes positioning the conduit in the system. The conduit is positioned, attached, installed, located, and/or arranged in the system such that the conduit is pinched or a slight force is applied by the one or more force transmitting members and/or sensors. A fluid can be introduced into the conduit from a source and/or the fluid inside the conduit can be pressurized. As the fluid is pressurized, the circumference, diameter, and/or one or more portions of the external surface of the conduit may expand. The expansion of the conduit may apply a force, or increase an initial force, on the one or more force transmitting members and/or sensors. The one or more sensors are adapted to generate one or more electronic signals according to the force applied on the sensors from the expanding conduit. The one or more signals are transmitted to the controller for determining a pressure value of the fluid in the conduit. The controller may use a look-up table and/or one or more algorithms or equations for correlating the change in pressure applied on the sensors (and thus the corresponding electronic signal) to a pressure value. The pressure value can be displayed on a display.

As the pressure in the conduit is reduced, the circumference, diameter, and/or one or more portions of the external surface of the conduit decreases or shrinks from its expanded state. Accordingly, a lower pressure or force is applied by the conduit on the force transmitting member(s) and/or sensors. Accordingly, the sensors generate and transmit one or more electronic signals to the controller. The controller determines the fluid pressure in the conduit from these signals.

FIG. 1 illustrates a system 10. The system 10 comprises a base 12 and a pair of side walls 14, 16. The system 10 includes a pair of first sensors 18, 20, and a pair of second sensors 22, 24. The sensors 18, 20, 22, 24 are electrically connected by conductor wire 26 to a controller 28. The system 10 includes force transmitting members 30, 32. The force transmitting member 30 includes a pair of projections 34, 36, and the force transmitting member 32 includes a pair of projections 38, 40.

With continued reference to FIG. 1, a conduit 42 is positioned in the system 10 such that an external surface 44 of the conduit 42 is positioned against both force transmitting members 30, 32. A source 46 of fluid F is in communication with the conduit 42. As the pressure of the fluid F supplied to the conduit 42 is increased, the conduit 42 expands at least in direction 46. As a result of the expansion, the external surface 44 applies a force f on the pair of first sensors 18, 20 and applies a force f' on the pair of second sensors 22, 24. That is, the expanding conduit 42 applies force f on force transmitting member 30, and a force f' on force transmitting member 32. Force f may be the same as or different than force f'. Force f is transferred to sensor 18 by way of projection 34 and transferred to sensor 20 by way of projection 36. Force f' is transmitted to sensor 22 by way of projection 38 and to sensor 24 by way of projection 40. In response to the forces f, f', the sensors 18, 20, 22, 24 are adapted to generate one or more electrical signals that correspond to the forces f, f'. The one or more electrical signals from sensors 18, 20, 22, 24 are communicated to the controller 28 via conductor wire 26. The controller 28 is adapted to determine the fluid pressure inside the conduit 42 by converting the one or more electrical signals to a fluid pressure value. The determined fluid pressure is communicated from the controller 28 to a display 44 for displaying the determined fluid pressure.

FIG. 2 illustrates a system 10. The system 10 comprises a base 12 and a pair of side walls 14, 16. The system 10 includes a first sensor grouping, which comprises a pair of first sensors 18, 20, and a second sensor grouping comprising a pair of second sensors 22, 24. The sensors 18, 20 in the first sensor grouping are electrically connected by conductor wire 26 to a controller 28 in a first electrical circuit. The sensors 22, 24 in the second sensor grouping are electrically connected by a conductor wire 48 to the controller 28 in a second electrical circuit. The system 10 includes force transmitting members 30, 32. Force transmitting member 30 includes a pair of projections 34, 36, and force transmitting member 32 includes a pair of projections 38, 40.

With continued reference to FIG. 2, a conduit 42 is positioned in the system 10 such that an external surface 44 of the conduit 42 is positioned against both force transmitting members 30, 32. A source 46 of fluid F is in communication with the conduit 42. As the pressure of the fluid F supplied to the conduit 42 is increased, the conduit 42 expands in direction 46. As a result of the expansion, the external surface 44 applies a force f on the pair of first sensors 18, 20 and applies a force f' on the pair of second sensors 22, 24. That is, the expanding conduit 42 applies force f on force transmitting member 30, and a force f' on force transmitting member 32. Force f may be the same as or different than force f'. Force f is transferred to sensor 18 by way of projection 34 and transferred to sensor 20 by way of projection 36. Force f' is transmitted to sensor 22 by way of projection 38 and to sensor 24 by way of projection 40. In response to the force f, the sensors 18, 20 are adapted to generate one or more electrical signals that correspond to the force f. The one or more electrical signals from sensors 18, 20 are communicated to the controller 28 via conductor wire 26. In response to the force f', the sensors 22, 24 are adapted to generate one or more electrical signals that correspond to the force f'. The one or more electrical signals from sensors 22, 24 are communicated to the controller 28 via conductor wire 48. The controller 28 determines the fluid pressure inside the conduit 42 by converting the one or more electrical signals in a fluid pressure value. The determined fluid pressure is communicated from the controller 28 to a display 44 for displaying the determined fluid pressure.

FIG. 3 illustrates a system 10. The system 10 comprises a base 12 and a pair of side walls 14, 16. The system 10 includes a pair of first sensors 18, 20, and a pair of second sensors 22, 24. Sensor 18 is electrically connected by conductor wire 52 to a controller 28 in a first electrical circuit. Sensor 20 is electrically connected by conductor wire 26 to the controller 28 in a second electrical circuit. Sensor 22 is electrically connected by conductor wire 50 to the controller 28 in a third electrical circuit. Sensor 24 is electrically connected by conductor wire 48 to the controller 28 in a fourth electrical circuit. The system 10 includes force transmitting members 30, 32. Force transmitting member 30 includes a pair of projections 34, 36, and force transmitting member 32 includes a pair of projections 38, 40.

With continued reference to FIG. 3, a conduit 42 is positioned in the system 10 such that an external surface 44 of the conduit 42 is positioned against both force transmitting members 30, 32. A source 46 of fluid F is in communication with the conduit 42. As the pressure of the fluid F supplied to the conduit 42 is increased, the conduit 42 expands in direction 46. As a result of the expansion, the external surface 44 applies a force f on the pair of first sensors 18, 20 and applies a force f'0 on the pair of second sensors 22, 24. That is, the expanding conduit 42 applies force f on force transmitting member 30, and a force f' on force transmitting member 32. Force f is transmitted to sensor 18 by way of projection 34 and to sensor 20 by way of projection 36. Force f' is transmitted to sensor 22 by way of projection 38 and to sensor 24 by way of projection 40. In response to the force f, the sensors 18, 20 are adapted to generate one or more electrical signals that correspond to the force f. The one or more electrical signals from sensors 18, 20 are communicated to the controller 28 via the respective conductor wires 52, 26. In response to the force f', the sensors 22, 24 are adapted to generate one or more electrical signals that correspond to the force f'. The one or more electrical signals from sensors 22, 24 are communicated to the controller 28 via the respective conductor wires 50, 48. The controller 28 determines the fluid pressure inside the conduit 42 by converting the one or more electrical signals in a fluid pressure value. The determined fluid pressure is communicated from the controller 28 to a display 44 for displaying the determined fluid pressure.

Figure 4:
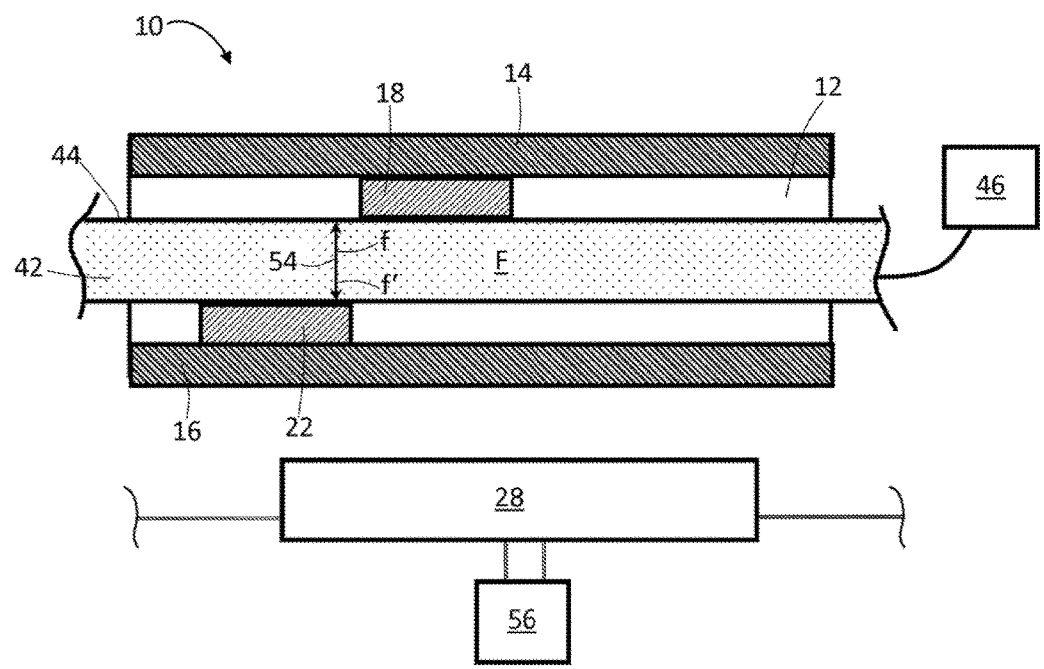
FIG. 4 is a schematic of the system according to the teachings herein.

FIG. 4 illustrates a system 10. The system 10 comprises a base 12 and a pair of opposing side wails 14, 16. The system 10 includes a pair of sensors 18, 22. The sensors 18, 22 are spaced apart and staggered, meaning the sensors 18, 22 are not located directly across from one another like in the preceding FIGS. 1-3. While not shown in this figures, the sensors 18, 22 are electrically connected by one or more conductor wires to a controller 28. Each of the sensors 18, 22 can be electrically connected to the controller 28 as illustrated in FIG. 3, or the sensors 18, 22 can be connected to the controller 28 in series as illustrated in FIG. 1. As illustrated in this figure, the system 10 may be free of force transmitting members. Alternatively, the system 10 may include one force transmitting member, for example either force transmitting member 30 or 32 from one of the preceding figures.

With continued reference to FIG. 4, a conduit 42 is positioned. In the system 10 such that an external surface 44 of the conduit 42 is positioned against the sensors 18, 22. A source 46 of fluid F is in communication with the conduit 42. As the pressure of the fluid F supplied to the conduit 42 is increased, the conduit 42 expands in direction 46. As a result of the expansion, the external surface 44 applies a force f on sensor 18, and applies a force f' on sensor 22. In response to the force f, the sensors 18, 22 are adapted to generate one or more electrical signals that correspond to the forces f, f'. The one or more electrical signals from sensors 18, 22 are communicated to the controller 28. The controller 28 is adapted to determine the fluid pressure inside the conduit 42 by converting the one or more electrical signals in a fluid pressure value. The determined fluid pressure can be communicated from the controller 28 to a display 44 for displaying the determined fluid pressure.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x"in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

LISTING OF REFERENCE NUMERALS

10 system
12 base
14 side wall
16 side wall
18 sensor
20 sensor
22 sensor
24 sensor
26 conductor wire
28 controller
30 force transmitting member
32 force transmitting member
34 projection
36 projection
38 projection
40 projection
42 conduit
44 external surface
46 expanding conduit
48 conductor wire
50 conductor wire
52 conductor wire

The invention claimed is:

1. A method of determining fluid pressure inside a conduit, the method comprising:
   a) positioning the conduit in a surgical system, the surgical system comprising:
      i) a pair of first sensors;
      ii) a pair of second sensors;
      iii) a first member comprising a pair of first projections; and
      iv) a second member comprising a first of second projections, the second member is spaced apart from the first member defining a space therebetween;
   wherein the conduit is positioned in the space between the first member and the second member;
   wherein the conduit is configured to expand in response to an increase in the fluid pressure inside the conduit, which causes the conduit to apply a force on the first member, the second member, or both, which then causes one or both of the first member and the second member to move away from each other and apply a force on the pair of first sensors, the pair of second sensors, or both via the corresponding pair of first projections, the pair of second projections, or both,
   b) generating one or more electrical signals with the pair of first sensors, the pair of second sensors, or both, the one or more electrical signals corresponding to the force applied on the pair of first sensors, the pair of second sensors or both; and
   c) determining the fluid pressure inside the conduit by converting the one or more electrical signals into a fluid pressure value through a controller.

2. The method of claim 1, wherein the controller is electrically connected in series with both the pair of first sensors and the pair of second sensors in a single electrical circuit.

3. The method of claim 1, wherein the controller is electrically connected in series with the pair of first sensors in a first electrical circuit, and the controller is electrically connected in series with the pair of second sensors in a separate electrical circuit.

4. The method of claim 1, wherein the controller is electrically connected to each sensor in the pair of first sensors via individual electrical circuits, and the controller is electrically connected to each sensor in the pair of second sensors via individual electrical circuits.

5. The method of claim 1, wherein both of the pair of first projections extend from the first member in a first direction, and both of the pair of second projections extend from the second member in a second direction that is opposite the first direction.

6. A surgical system, comprising:
a base;
a first wall extending from the base;
a second wall extending from the base, the second wall is spaced apart from the first wall;
a first sensor supported on the first wall;
a second sensor supported on the second wall;
a first member comprising a first projection extending towards the first sensor;
a second member comprising a second projection extending towards the second sensor; and
a controller;
wherein the first member and the second member are spaced apart from one another so that a space is defined between the two members;
wherein an expandable conduit is configured to be positioned in the space between the two members, the conduit is configured to expand in response to an increase in fluid pressure inside the conduit, which causes the conduit to move one or both of the first member and the second member away from one another, which causes one or both of the first member and the second member to apply a force on one or both of the first sensor and the second sensor via the corresponding first and second projections;
wherein the first sensor, the second sensor, or both are configured to generate one or more electrical signals in response to the force applied thereon; and
wherein the one or more electrical signals are communicated to the controller, and the controller converts the one or more electrical signals into a fluid pressure value.

7. The surgical system of claim 6, wherein the surgical system comprises a third sensor supported on the first wall and a fourth sensor supported on the second wall, the first member comprising a third projection extending towards the third sensor, and the second member comprising a fourth projection extending towards the fourth sensor.

8. The surgical system of claim 7, wherein all of the projections extend in a direction that is generally perpendicular to a longitudinal axis of the conduit.

9. The surgical system of claim 7, wherein the controller is
electrically connected in series with the first, second, third, and fourth sensors.

10. The surgical system of claim 7, wherein the controller is electrically connected in series with the first and third sensors in a first circuit, and electrically connected in series with the second and fourth sensors in a second discrete circuit.

11. The surgical system of claim 6, wherein the first sensor is laterally offset relative to the second sensor.

12. A method of determining pressure of a fluid in a conduit, the method comprising:
a) attaching the conduit to a surgical system, the system comprising:
i) a first sensor;
ii) a second sensor;
iii) first force transferring member; and
iv) a second force transferring member;
b) determining a pressure of the fluid in the conduit;
wherein the conduit is configured to expand in response to an increase in the pressure of the fluid inside the conduit and apply a force on one or both of the first force transferring member and the second force transferring member so that the one or both of the first force transferring member and the second force transferring member move away from one another and apply a force on one or both of the first sensor and the second sensor; and
wherein one or more electrical signals corresponding to the force applied on one or both of the first sensor and the second sensor are communicated from the respective first sensor and the second sensor to a controller, that is configured to correspond the one or more electrical signals to the pressure of the fluid in the conduit.

13. The method of claim 12, wherein the first sensor comprises a pair of first sensors, and the second sensor comprises a pair of second sensors.

14. The method of claim 13, wherein the pair of first sensors are electrically connected in series with the controller, and the pair of second sensors are electrically connected in series with the controller in a separate circuit.

15. The method of claim 13, wherein the pair of first sensors are electrically connected in series with the controller, and the pair of second sensors are electrically connected in series with the controller in a common circuit with the pair of first sensors.

16. The method of claim 13, wherein each sensor of the pair of first sensors are individually electrically connected to the controller, and each sensor of the pair of second sensors are individually electrically connected to the controller.

17. The method of claim 13, wherein the first force transferring member comprises two projections that extend towards each of the pair of first sensors, and the second force transferring member comprises two projections that extend towards each of the pair of second sensors, and
wherein the force is applied on each of the pair of first sensors and on each of the pair of second sensors with the corresponding two projections on the first and second members when the first force transferring member and the second force transferring member move away from each other.

18. The method of claim 12, wherein the first force transferring member comprises a first projection extending towards the first sensor, and the second force transferring member comprises a second projection extending towards the second sensor, and
wherein the force is applied on the first sensor and the second sensor with the corresponding first and second projections when the first force transferring member and the second force transferring member move away from each other.

19. The method of claim 12, wherein the first sensor is supported on a first wall of the surgical system, and the second sensor is supported on a second wall of the surgical system, the walls extend vertically from a base of the surgical system.

20. The method of claim 19, wherein the first sensor is laterally offset relative to the second sensor.

* * * * *